United States Patent [19]

Renga et al.

[11] 4,343,029
[45] Aug. 3, 1982

[54] ELECTRICAL DEVICE CONTAINING AN ARYL SULFIDE DIELECTRIC LIQUID

[75] Inventors: James M. Renga; Albert H. Emmons, both of Midland, Mich.

[73] Assignee: The Dow Chemical Company, Midland, Mich.

[21] Appl. No.: 187,689

[22] Filed: Sep. 16, 1980

Related U.S. Application Data

[63] Continuation-in-part of Ser. No. 78,318, Sep. 24, 1979, abandoned.

[51] Int. Cl.³ .......................... H01B 3/22; H01G 4/04
[52] U.S. Cl. .............................. 361/315; 174/17 LF; 252/571; 252/574; 361/327; 568/58
[58] Field of Search ............................. 252/574, 571; 174/17 LF; 361/315, 327; 568/58

[56] References Cited

U.S. PATENT DOCUMENTS

| | | | |
|---|---|---|---|
| 2,176,952 | 10/1939 | Berberich | 252/574 |
| 2,288,373 | 6/1942 | Smith et al. | 252/574 X |
| 2,410,714 | 11/1946 | Clark | 252/574 |
| 3,345,292 | 10/1967 | Neale et al. | 252/47 |
| 3,538,166 | 11/1970 | Campbell et al. | 260/609 |
| 3,706,805 | 12/1972 | Fujisawa et al. | 260/609 E |
| 4,097,912 | 6/1978 | Lapp et al. | 361/318 |
| 4,121,275 | 10/1978 | Ross et al. | 361/315 X |
| 4,147,646 | 4/1979 | Cappo | 361/327 X |
| 4,203,145 | 5/1980 | Klein et al. | 361/317 |

FOREIGN PATENT DOCUMENTS 1583819 12/1969 France .

*Primary Examiner*—Dennis L. Albrecht

[57] ABSTRACT

Capacitors and similar electrical devices containing a dielectric liquid have superior properties when the dielectric liquid is a polyalkylated diphenyl sulfide. Particularly good dielectric properties are provided when the liquid consists essentially of the mixed isomers obtained by reacting m-xylene or similar dialkylbenzene with $SCl_2$.

16 Claims, 2 Drawing Figures

ELECTRICAL DEVICE CONTAINING AN ARYL SULFIDE DIELECTRIC LIQUID

CROSS-REFERENCE TO RELATED APPLICATION

This application is a continuation-in-part of our earlier application Ser. No. 78,318 filed Sept. 24, 1979 and now abandoned.

BACKGROUND OF THE INVENTION

The invention relates to electrical devices containing a dielectric liquid such as capacitors and transformers wherein the dielectric liquid is essentially a particularly defined class of aromatic sulfides.

Until recent years, polychlorinated biphenyl (PCB) was widely used as a dielectric liquid in transformers and other such electrical devices. Although its physical and electrical properties made it a superior material for this kind of use, PCB was found to have highly undesirable biological effects and these and its resistance to degradation when it was allowed to contaminate the ground or bodies of water by spillage or by improper disposal caused a widespread search for other dielectric liquids with less objectionable properties.

Among the alternative liquids suggested for this use, chlorinated diphenyl oxides have many advantages in both their physical and their biological properties. However, concern about the biological effects of possible polychlorinated aromatic impurities in these materials has caused some delay and restriction in their use on a large scale.

Aromatic sulfones have also been proposed for use as dielectric liquids. These compounds have other disadvantages, however, including unusually high dielectric constants that may cause an unacceptably high level of electrical conductivity and also undesirably high melting or pour points. To avoid these disadvantages, various mixtures of aromatic sulfones with known dielectric liquids have been proposed. Since the suggested diluents usually include polychlorinated aromatic hydrocarbons, the original advantages of the sulfones as dielectric liquids are thus also diluted and lost.

Analogous aromatic sulfides are known and some of these have been proposed for use as functional fluids, for example, as synthetic lubricants, hydraulic fluids, and damping fluids. Fujisawa et al., U.S. Pat. No. 3,706,805 (see also related French Pat. No. 1,583,819) describes the preparation of aryl-sulfides by the reaction of various substituted aromatic hydrocarbons with a sulfur chloride in the presence of a metal or metal halide catalyst. The principal utilities taught for the resulting products are as fungicides and herbicides. Campbell et al., U.S. Pat. No. 3,538,166 describes another method for the preparation of aromatic and heterocyclic sulfides. The compounds shown are mostly halogenated and polynuclear sulfides and mixed ether-sulfides. The products are broadly described as functional fluids including dielectric fluids. However, the compounds shown typically have relatively high melting or pour points and some are solids at room temperature.

SUMMARY OF THE INVENTION

It has now been found that electrical devices that contain a dielectric liquid such as capacitors and transformers have advantageous electrical and other properties when the dielectric liquid comprises a particular class of alkylated diphenyl sulfides of the formula

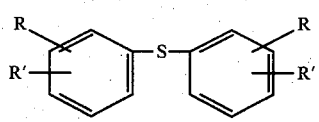

wherein each R is independently an alkyl group of 1 to about 20 carbon atoms and each R' is selected from the group consisting of hydrogen and the alkyl groups as defined for R. Preferably, alkyl groups represented by R and R' are lower alkyl groups, that is, groups containing 1 to about 4 carbon atoms.

DETAILED DESCRIPTION OF THE INVENTION

Figure 1:
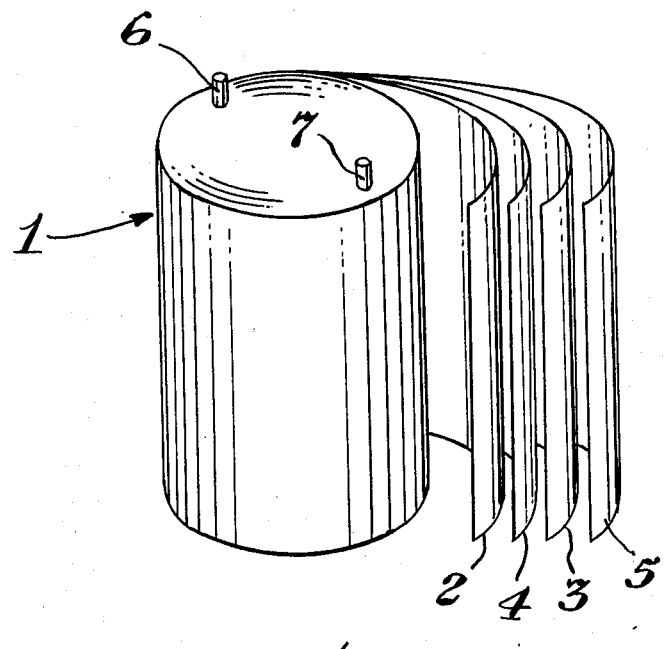
FIG. 1 is a perspective view of a partially wound capacitor pack.

A typical capacitor illustrative of the present invention has the general structure shown in FIG. 1 where the capacitor pack or reel 1 contains plates wound on top of each other in a roll having separated electrode foils or armatures 2 and 3 and intermediate separator sheets 4 and 5. The electrodes 6 and 7 are connected to the electrode foils 2 and 3, both electrodes and electrode foils being of an electrically conductive material such as copper, aluminum, or the like. The foils 2 and 3 may be in the form of thin, flat sheets which may alternatively have surface irregularities such as indentations on one side with corresponding elevations on the other side as shown in U.S. Pat. No. 3,746,953.

The separator sheets 4 and 5 are usually made of paper, a polymer film, or a combination of these such as a paper-polymer film laminate. A polymer film separator sheet may be of porous or nonporous film or it may have surface irregularities to promote a wicking action on the dielectric fluid with which the capacitor is impregnated. Suitable polymer films include films made of polyolefin, for example, polypropylene or polyethylene, and also polyester and polycarbonate films.

An electrode foil 2-separator sheet 4 pair may constitute a unitary sheet such as a metal foil-paper laminate. Two separator sheets may be used for each metal foil sheet.

Figure 2:
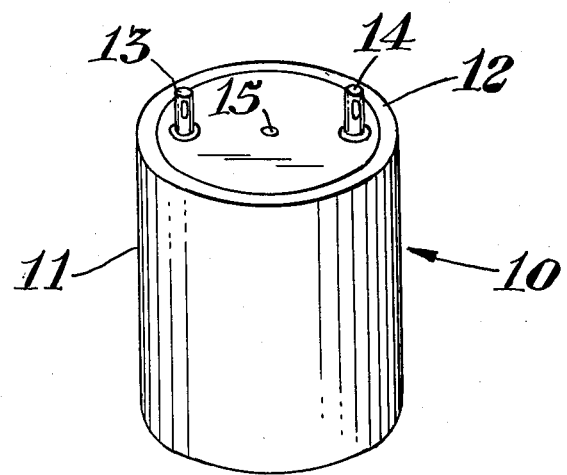
FIG. 2 is a perspective view of an assembled capacitor comprising the capacitor pack and an impregnating dielectric liquid.

FIG. 2 shows an assembled capacitor 10 containing a wound capacitor pack as shown in FIG. 1. The assembled unit consists of a container 11 having a sealed cover 12, a pair of terminals 13 and 14 extending through the cover 12 and insulated from it, and a small hole 15 in the cover 12 for drying the capacitor pack and for inserting the dielectric liquid (not shown) which impregnates the capacitor pack and fills the remaining space within the container 11 not taken up by the capacitor pack. Terminals 13 and 14 are connected inside the container 11 with electrodes 6 and 7 shown in FIG. 1.

The capacitor unit 10 is impregnated and filled with the dielectric liquid by conventional procedures whereby the unit is dried at an elevated temperature and reduced pressure using the open hole 15 as a vent. The evacuated and dried capacitor unit 10 is typically then impregnated and filled with the purified dielectric liquid under conditions such that thorough impregnation is obtained, for example, by standing for a period of time and, optionally, by total immersion of the capacitor in the liquid. After complete filling and impregnation, the vent hole 15 is closed with solder or other suitable sealing composition. The sealed capacitor may be heated to raise the internal pressure for optimum impregnation.

The alkylated diphenyl sulfides as defined above are preferably prepared by reacting an appropriate alkylbenzene or dialkylbenzene with $SCl_2$ in the presence of iron, ferric chloride, or other metal halide known to promote the reaction. The sulfide product of this reaction is a mixture of isomers, usually consisting largely of one isomer with the remainder essentially the next favored position isomer and only minor amounts of other isomers. If mixed isomers of a dialkylbenzene or a mixture of a monoalkylbenzene and a dialkylbenzene is used as the aromatic hydrocarbon starting material, a more complex mixture of isomeric or homologous alkylated diphenyl sulfides is obtained as the sulfide product of the reaction. Analyses of the products indicate that small amounts of disulfide or higher polysulfides are often present as by-products of the reaction. The proportion of structural isomers or relative amounts of polysulfide by-products in these products is generally of noncritical consequence in their use as dielectric liquids in the devices of the present invention.

These alkylated diphenyl sulfides as defined above are typically nearly colorless to light yellow-orange liquids at room temperature. Most remain liquid at temperatures as low as $-30°$ C. or lower and have boiling points at atmospheric pressure in the approximate range of 365° C.–445° C. Their dielectric constants range from about 3.8 to about 6.3 and their electrical dissipation factors are ordinarily very low.

The dielectric liquid composition may include up to about 25 percent by weight of one or more known dielectric liquids as diluent in order to obtain particular physical or dielectric properties. Such diluents include hydrocarbon oils, monochlorinated diphenyl ether and alkyl-substituted derivatives thereof, aryl sulfones, and the like. The dielectric liquid may also include conventionally used additives for such compositions such as antioxidants and epoxide scavengers for halogen-containing impurities or decomposition products although an antioxidant is ordinarily not needed because the aryl sulfides themselves have antioxidant properties. Epoxide scavengers include bis(3,4-epoxy-6-methylcyclohexylmethyl)adipate, 1,2-epoxy-3-phenoxypropane, 1-epoxyethyl-3,4-epoxycyclohexane, and the diglycidyl ether of bisphenol A.

A preferred method for the preparation of the alkylated diphenyl sulfide dielectric liquid of the present invention is described in the following examples.

EXAMPLES 1–8—Preparation of Alkyl-Substituted Diphenyl Sulfides

Isomeric mixtures of various lower alkyl-substituted diphenyl sulfides were prepared by reacting a lower alkyl-substituted benzene with $SCl_2$ in the presence of iron powder and distilling the reaction product to obtain the purified aryl sulfide product. The reaction was carried out by adding a mole of $SCl_2$ dropwise over a period of 2–6 hours to a stirred mixture of 2–5 moles of the alkylated benzene and about 0.5 mole percent of iron powder based on the alkylated benzene at an initial temperature of about 50° C. A Teflon-shielded reaction flask was used to avoid light-induced disproportionation of the $SCl_2$ and the HCl by-product was flushed from the mixture as it was produced using a nitrogen bubbler. After a short induction period, the reaction proceeded exothermically at 50° C.–55° C. and the reaction mixture was finally heated at 100° C. to complete the reaction. The reaction mixture was then distilled under reduced pressure to obtain the mixed isomeric sulfide product.

Similar results were obtained when the iron catalyst was replaced by a comparable amount of $AlCl_3$. Other suitable reaction catalysts include $Al_2S_3$, FeS, ZnS, NiS, and CoS.

The best yields of sulfide product were obtained when the alkylated benzene starting material was a meta-dialkylbenzene. For example, product yields of about 60–80 percent were obtained using m-xylene and m-diethylbenzene. The sulfide products obtained from these starting materials were typically largely the bis-(2,4-dialkylphenyl)sulfide. For example, the product obtained using m-xylene was about 9 parts bis(2,4-dimethylphenyl)sulfide and one part 2,4-dimethylphenyl 2,6-dimethylphenyl sulfide.

Physical properties, the dielectric constant (DK) and the electrical dissipation factor (DF) of the distilled aryl sulfide products were determined at 20° C. and these are listed in the table. The electrical constants were determined by ASTM method 924 for electrical insulating liquids. In the table Me=methyl, Et=ethyl, iPr=isopropyl, and tBu=tertiary butyl. All of these products had relatively high flash points and remained liquid at very low temperatures, these properties for the other products being similar to those indicated specifically for the products of Examples 2 and 8.

TABLE

| Example No. | R | R' | BP °C. (760 mm) | DK | DF ($10^4$ Hz) | Other Properties |
|---|---|---|---|---|---|---|
| 1 | 1-Me | 2-Me | 380–390 | 6.24 | 0.06 | |
| 2 | 1-Me | 3-Me | 365–375 | 3.93 | 0.001 | flash point 176° C., liquid at $-30°$ C. |
| 3 | Me (mix)[1] | Me | 390–395 | 4.15 | 0.0003 | |
| 4 | 1-Et | 3-Et | 435–440 | 3.95 | 0.002 | |
| 5 | Et (mix)[2] | Et | 435–440 | 3.92 | 0.0003 | |
| 6 | 1-Me | 4-tBu | 435–445 | 3.85 | 0.001 | |
| 7 | iPr (mix)[3] | iPr | 435–445 | 3.96 | 0.0004 | |
| 8 | iPr | H | 390–400 | 5.02 | 0.004 | liquid at $-30°$ C. |

[1]61:23:15 meta:para:ortho mixture
[2]70:30 meta:para mixture
[3]70:30 meta:para mixture

We claim:
1. In an electrical device containing a dielectric liquid as the impregnating agent, the improvement wherein the dielectric liquid consists essentially of at least one compound of the formula

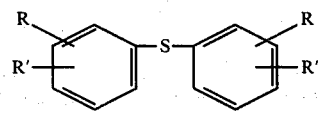

wherein each R is independently an alkyl group of one to about 20 carbon atoms and each R' is independently hydrogen or an alkyl group as defined for R.

2. The electrical device of claim 1 wherein the formula defines a mixture of isomeric compounds.

3. The electrical device of claim 1 wherein R is an alkyl group of one to about four carbon atoms and R' is hydrogen or R.

4. The electrical device of claim 3 wherein R and R' both represent methyl groups.

5. A capacitor according to claim 1, said capacitor comprising a plurality of alternately spaced apart electrode foil sheets and separator sheets, said sheets having said dielectric liquid between them.

6. The capacitor of claim 5 wherein the dielectric liquid consists essentially of a mixture of isomeric compounds of the defined formula.

7. The capacitor of claim 5 wherein R is an alkyl group of one to about four carbon atoms and R' is hydrogen or R.

8. The capacitor of claim 7 wherein R and R' are both methyl groups.

9. The electrical device of claim 3 wherein R and R' both represent ethyl groups.

10. The electrical device of claim 3 wherein R and R' both represent isopropyl groups.

11. The electrical device of claim 3 wherein R represents a methyl group and R' represents a tertiary butyl group.

12. The electrical device of claim 3 wherein R represents an isopropyl group and R' represents hydrogen.

13. The capacitor of claim 7 wherein R and R' both represent ethyl groups.

14. The capacitor of claim 7 wherein R and R' both represent isopropyl groups.

15. The capacitor of claim 7 wherein R represents a methyl group and R' represents a tertiary butyl group.

16. The capacitor of claim 7 wherein R represents an isopropyl group and R' represents hydrogen.

* * * * *